(12) United States Patent
Zhao et al.

(10) Patent No.: US 10,653,653 B2
(45) Date of Patent: May 19, 2020

(54) SALTS OF 5-AMINOLEVULINIC ACID AND DERIVATIVES

(71) Applicants: Ming Zhao, Darien, IL (US); Li-Ming Zhou, Darien, IL (US)

(72) Inventors: Ming Zhao, Darien, IL (US); Li-Ming Zhou, Darien, IL (US)

(*) Notice: Subject to any disclaimer, the term of this patent is extended or adjusted under 35 U.S.C. 154(b) by 0 days.

(21) Appl. No.: 16/071,485

(22) PCT Filed: Jan. 24, 2017

(86) PCT No.: PCT/US2017/014791
§ 371 (c)(1),
(2) Date: Jul. 20, 2018

(87) PCT Pub. No.: WO2017/132178
PCT Pub. Date: Aug. 3, 2017

(65) Prior Publication Data
US 2019/0022044 A1  Jan. 24, 2019

Related U.S. Application Data

(60) Provisional application No. 62/286,977, filed on Jan. 26, 2016.

(30) Foreign Application Priority Data

Jul. 20, 2016 (CN) .......................... 2016 1 0568868

(51) Int. Cl.

| | | |
|---|---|---|
| *A61K 31/197* | (2006.01) | |
| *A61K 41/00* | (2020.01) | |
| *A61K 47/12* | (2006.01) | |
| *A61K 45/06* | (2006.01) | |
| *C07C 53/16* | (2006.01) | |
| *C07C 229/22* | (2006.01) | |
| *A61K 9/00* | (2006.01) | |
| *A61K 9/06* | (2006.01) | |
| *A61K 9/08* | (2006.01) | |
| *A61P 17/10* | (2006.01) | |
| *A61P 17/06* | (2006.01) | |
| *A61P 35/00* | (2006.01) | |

(52) U.S. Cl.
CPC ............ *A61K 31/197* (2013.01); *A61K 9/006* (2013.01); *A61K 9/0009* (2013.01); *A61K 9/0014* (2013.01); *A61K 9/06* (2013.01); *A61K 9/08* (2013.01); *A61K 41/0061* (2013.01); *A61K 45/06* (2013.01); *A61K 47/12* (2013.01); *A61P 17/06* (2018.01); *A61P 17/10* (2018.01); *A61P 35/00* (2018.01); *C07C 53/16* (2013.01); *C07C 229/22* (2013.01)

(58) Field of Classification Search
CPC .. A61K 31/197; A61K 41/0061; A61K 47/12; A61K 9/0009; A61K 9/0014; A61K 9/06; A61K 9/08; A61K 45/06; C07C 229/22; C07C 53/16; A61P 17/06; A61P 17/10; A61P 35/00

See application file for complete search history.

(56) References Cited

U.S. PATENT DOCUMENTS

| | | | |
|---|---|---|---|
| 5,273,982 A | 12/1993 | Alig et al. | |
| 5,661,111 A | 8/1997 | Kuramochi et al. | |
| 6,011,173 A * | 1/2000 | Labat ................... | C07C 327/06 562/26 |
| 6,034,267 A | 3/2000 | Gierskcky et al. | |
| 6,269,818 B1 | 8/2001 | Lui et al. | |
| 6,492,420 B2 | 12/2002 | Gierskcky et al. | |
| 6,723,750 B2 | 4/2004 | Voet | |
| 7,154,001 B2 | 12/2006 | Hadfield et al. | |
| 7,217,736 B2 | 5/2007 | Klaveness | |
| 7,888,526 B2 | 2/2011 | Braenden et al. | |
| 7,964,630 B2 | 6/2011 | Imfelt et al. | |
| 8,173,839 B2 | 5/2012 | Tachiya et al. | |
| 8,692,014 B2 | 4/2014 | Braenden et al. | |
| 9,249,086 B2 | 2/2016 | Braenden et al. | |
| 2003/0125388 A1 | 7/2003 | Gander et al. | |
| 2004/0147501 A1* | 7/2004 | Dolmans .............. | A61K 31/555 514/185 |
| 2005/0124638 A1* | 6/2005 | Swayze ............. | A61K 31/4188 514/267 |
| 2006/0265028 A1 | 11/2006 | Houle et al. | |
| 2007/0225518 A1 | 9/2007 | Malik et al. | |
| 2008/0064752 A1* | 3/2008 | Braenden ........... | A61K 41/0061 514/561 |
| 2014/0249217 A1* | 9/2014 | Rii ....................... | A61K 31/197 514/502 |

(Continued)

FOREIGN PATENT DOCUMENTS

| | | |
|---|---|---|
| AU | 2003247515 A1 | 12/2003 |
| AU | 2013298525 B2 | 12/2017 |

(Continued)

OTHER PUBLICATIONS

Loh, C.S. et al. (1992). "Photodynamic Therapy of the Normal Rat Stomach: A Comparative Study between Di-Sulphonated Aluminium Phthalocyanine and 5-Aminolaevulinic Acid," Br. J. Cancer 66:452-462.

Svanberg, K. et al. (Jun. 1994). "Photodynamic Therapy of Non-Melanoma Malignant Tumours of the Skin Using Topical δ-Amino Levulinic Acid Sensitization and Laser Irradiation," Br. J. Dermatol. 130(6):743-751.

Karrer, S. et al. (Feb. 1997). "Topical Application of a First Porphycene Dye for Photodynamic Therapy—Penetration Studies in Human Perilesional Skin and Basal Cell Carcinoma," Arch. Dermatol. Res. 289(3):132-137.

Gadmar, Ø.B. et al. (Jul. 2002). "The stability of 5-Aminolevulinic Acid in Solution," J. Photochem. Photobiol. B. 67(3):187-193.

(Continued)

*Primary Examiner* — Sarah Pihonak

(57) ABSTRACT

The present disclosure provides new salts of 5-aminolevulinic acid (5-ALA) and new salts of 5-ALA esters, their preparation, formulation and use as photosensitizing agents in photodynamic therapy, diagnosis and cosmetic cares.

13 Claims, No Drawings

(56) References Cited

U.S. PATENT DOCUMENTS

2014/0315888 A1* 10/2014 Ho ............... C07D 487/14
514/210.21

FOREIGN PATENT DOCUMENTS

| | | |
|---|---|---|
| CN | 103265444 B | 11/2014 |
| CN | 104478991 B | 6/2018 |
| EP | 2407151 A1 | 1/2012 |
| EP | WO2014/020164 A1 | 2/2014 |
| GB | WO2002010120 A1 | 2/2002 |
| GB | 0406917 | 4/2004 |
| JP | 2896963 B2 | 5/1999 |
| JP | 5645104 B2 | 12/2014 |

OTHER PUBLICATIONS

Grapengiesser, S. et al. (Sep. 2002). "Pain Caused by Photodynamic Therapy of Skin Cancer," Clin. Exp. Dermatol. 27(6):493-497.

Kelty, C.J. et al. (2002). "The Use of 5-Aminolevulinic Acid as a Photosensitiser in Photodynamic Therapy and Photodiagnosis," Photochem. Photobiol. Sci. 1(3):158-68.

Jichlinski, P. et al. (Jul. 2003). "Hexyl Aminolevulinate Fluorescence Cystoscopy: New Diagnostic Tool for Photodiagnosis of Superficial Bladder Cancer—a Multicenter Study," J. Urol. 170(1):226-229.

Dover, J.S. et al. (Oct. 2005). "Topical 5-Aminolevulinic Acid Combined with Intense Pulsed Light in the Treatment of Photoaging," Arch. Dermatol. 141(10):1247-1252.

Vallinayagam, R. (2007). "Synthesis of Novel Prodrugs for Targeted Photodynamic Therapy", Dissertation. 302 pages.

Chen, K. et al. (Mar. 2007), "Comparative Study of Photodynamic Therapy vs CO2 Laser Vaporization in Treatment of Condylomata Acuminata: a Randomized Clinical Trial," Br. J. Dermatol. 156(3):516-520.

Zane, C. et al. (Mar. 2007). "Clinical and Echographic Analysis of Photodynamic Therapy Using Methylaminolevulinate as Sensitizer in the Treatment of Photodamaged Facial Skin," Lasers Surg. Med. 39(3):203-209.

Mavilia, L, et al. (Oct. 2007). "Photodynamic Therapy of Acne Using Methyl Aminolaevulinate Diluted to 4% Together with Low Doses of Red Light," Br. J. Dermatol. 157(4):810-811.

Vallinayagam, R. et al. (2008), "Glycoside Esters of 5-Aminolevulinic Acid for Photodynamic Therapy of Cancer," Bioconjugate Chem. 19(4):821-839.

Kemmner, W. et. al. (Feb. 2008). "Silencing of Human Ferrochelatase Causes Abundant Protoporphyrin-IX Accumulation in Colon Cancer," FASEB J. 22(2):500-509.

Fotinos, N. (Apr. 2008). "Effects on Gram-Negative and Gram-Positive Bacteria Mediated by 5-Aminolevulinic Acid and 5-Aminolevulinic Acid Derivatives," Antimicrob. Agents Chemother. 52(4):1366-1373.

Krammer, B. et al. (Nov. 2008). "ALA and its Clinical Impact, from Bench to Bedsid," Photochem. Photobiol. Sci. 7:283-289.

Choudhary, S. et al. (Nov. 2009), "Lasers in Medical Science Photodynamic Therapy in Dermatology: A Review," Lasers in Med. Sci. 24(6): 971-980.

Sakamoto, F.H. et al. (Aug. 2010). "Photodynamic therapy for Acne Vulgaris: A Critical Review from Basics to Clinical Practice: Part II. Understanding Parameters for Acne Treatment with Photodynamic Therapy," J. Am. Acad. Dermatol. 63(2):195-211.

Forster, B. et al. (Sep. 2010). "Penetration Enhancement of Two Topical 5-Aminolaevulinic Acid Formulations for Photodynamic Therapy by Erbium:YAG Laser Ablation of the Stratum Corneum: Continuous Versus Fractional Ablation," Exp. Dermatol. 19(9):806-812.

Iwai, R. et al. (May 2011), "Synthesis and Antibacterial Activity of Alaremycin Derivatives for the Porphobilinogen Synthase" Bioorg. Med. Chem. Lett. 21(10):2812-2815.

Calzavara-Pinton, P. et al. (May-Jun. 2012). "Photodynamic Antifungal Chemotherapy," Photochem. Photobiol. 88(3):512-522.

Wan, M.T. et al. (May 21, 2014). "Current Evidence and Applications of Photodynamic Therapy in Dermatology," Clin. Cosmet. Investig. Dermatol. 7:145-163.

Avci, P. et al. (Sep. 2014). "Photodynamic Therapy: One Step Ahead with Self-Assembled Nanoparticles," J. Biomed. Nanotechnol. 10(9):1937-1952.

Agarwal, N. et al. (May 2015). "Therapeutic Response of 70% Trichloroacetic Acid CROSS in Atrophic Acne Scars," Dermatol. Surg. 41(5):597-604.

Nuzzo, S.D, et al. (Sep. 2015), "Comparative Study of Trichloroacetic Acid vs. Photodynamic Therapy with Topical 5-Aminolevulinic Acid for Actinic Keratosis of the Scalp," Photodermatol. Photoimmunol. Photomed. 31(5):233-238.

Carrasco, E. et al. (Nov. 2015). "Photoactivation of ROS Production In Situ Transiently Activates Cell Proliferation in Mouse Skin and in the Hair Follicle Stem Cell Niche Promoting Hair Growth and Wound Healing," J. Invest. Dermatol. 135(11):2611-2622.

Meguid, A.M.A. (Dec. 2015). "Trichloroacetic Acid Versus Salicylic Acid in the Treatment of Acne Vulgaris in Dark-Skinned Patients," Dermatol. Surg. 41(12):1398-1404.

Fonda-Pascual, P. (Oct. 15, 2016), "In Situ Production of ROS in the Skin by Photodynamic Therapy as a Powerful Tool in Clinical Dermatology," Methods 109:190-202.

* cited by examiner

SALTS OF 5-AMINOLEVULINIC ACID AND DERIVATIVES

CROSS-REFERENCE TO RELATED APPLICATION AND INCORPORATION BY REFERENCE

The present application is a U.S. National Phase filing of International Application Serial No. PCT/US2017/014791 filed 24 Jan. 2017 and claims priority to U.S. Provisional Patent Application No. 62/286,977, filed Jan. 26, 2016, and Chinese Application No. 201610568868.0, filed Jul. 20, 2016, the entireties of which are hereby incorporated by reference.

FIELD

The present disclosure relates to salts of 5-aminolevulinic acid (5-ALA) and salts of 5-ALA esters, their preparation, formulation and use as photosensitizing agents in photodynamic therapy, diagnosis or cosmetic treatment.

BACKGROUND

Photodynamic therapy (PDT, also known as photochemotherapy) is a therapeutic technique that uses a photosensitizing agent and a particular light source to activate the photosensitizer. Upon exposure to visible light, the photosensitizer is activated to high energy states and further reacts with oxygen or transfer its energy to oxygen molecules to create reactive oxygen species (ROS), such as singlet oxygen or free oxygen radicals. ROS are highly cytotoxic leading to apoptosis or necrosis of malignant and abnormal cells. The activated photosensitizer can also return to a lower energy level partly by emitting red fluorescence, which can be used for diagnostic purposes. PDT has a wide range of clinical applications in fields such as dermatology, diagnosis and cosmetic treatment.

Among the most commonly used photosensitizers or precursors in PDT are 5-aminolevulinic acid (5-ALA) and its two esters, 5-methylaminolevulinate (5-MAL) and 5-hexylaminolevulinate (5-HAL). Most cells of the human body can absorb and transform 5-ALA or its esters to photoactivatable porphyrins in particular protoporphyrin IX (PpIX), which is a very potent photosensitizer, via the porphyrin biosynthetic pathway. Studies have confirmed that cancerous, precancerous or diseased cells tend to accumulate more porphyrins than normal cells. This selectivity has been contributed to the dysfunction of abnormal cells or tissue, including reduced ferrochelatase in neoplasms (Kemmner et al, FASEB J, 2008, 22:500-509) or enhanced permeability and retention effects (Avci et al, J Biomed Nanottechnl, 2014, 10(9)1937-1952).

PDT using 5-ALA and its esters has proven to be a safe and effective therapeutic strategy with excellent cosmetic outcomes (Fonda-Pascual et al, Methods, 2016, 109, 190-202) in the treatment of certain cancers, pre-cancerous disorders, non-cancerous lesion and in cancer diagnoses (Jichlinski et al, J Urol, 2003, 170: 226-9). Since these agents are unstable and prone to polymerization, they are provided as hydrochloride salts in clinical applications. Levulan® (20% 5-aminolevulinic acid hydrochloride, DUSA Pharmaceuticals, Wilmington, Mass., USA) is approved for the treatment of actinic keratosis in US and ALA (20% 5-ALA hydrochloride, Fudan-Zhangjiang Bio-Pharma, Shanghai, China) for the treatment of external condyloma acuminatum in China. Metvix® (16% 5-MAL hydrochloride, PhotoCure ASA, Oslo, Norway) is used for the treatment of actinic keratosis, superficial basal cell carcinoma and Bowen's disease. Hexvix® (5-HAL hydrochloride, PhotoCure ASA, Oslo, Norway) is a highly potent photosensitizer for the diagnoses of bladder cancer.

5-ALA and 5-MAL are also currently in multiple clinical trials and in off-label use for the treatment of moderate to severe acne vulgaris (Mavilia et al, Br J Dematol, 2007, 157:779-846). In addition, preclinical and clinical PDT studies have shown that 5-ALA and its esters are effective to treat bacterial (Fotinos et al, Antimicrob Agents Chemother, 2008, 52:1366-1373) and fungal infections (Calzavara-Pinton et al, Photochem Photobiol, 2012, 88:512-522), inflammatory disorders (e.g. morphea, actinic cheiliti, acne) and infections associated with virus and cancers (e.g. viral warts).

Jeffry et al describe 5-ALA and its methyl ester as useful agents for photodynamic cosmetic treatment (Arch Dermatol, 2005 141:1247-1252). Carrasco et al demonstrate the ability of in situ ROS induced by 5-MAL-PDT to activate cell proliferation in mouse skin and in the hair follicle stem cell niche, promoting hair growth, tissue repair and wound healing (J Invest Dermatol, 2015, 135(11):2611-2622). All the references described herein are incorporated by reference.

However, hydrochloride salts of 5-ALA and its esters possess a number of undesirable properties, including skin irritation, inflammation and pain at the treatment site upon light exposure (Grapengiesser et al, Clin Exp Dermatol, 2002, 27:493-497), hygroscopic which may cause degradation during storage and instability in pharmaceutical formulations (Gadmar et al, J. Photochem. Photobiol B: Biol, 2002, 67:187-193). The other major limitation of topical 5-ALA and 5-MAL-PDT is the depth of irradiation and skin penetration of the drug. Inadequate skin penetration was considered to play a major role. Therefore, enhancing skin penetration of these agents would improve PDT effectiveness (Foster et al, Exp Dermatol, 2010, 19:806-12).

U.S. Pat. No. 8,692,014 describes that sulfonate salts of 5-ALA analogs exhibit reduced hydroscopicity and enhanced fluorescence production in cells in comparison with hydrochloride salts. U.S. Pat. No. 8,173,839 describes that 5-ALA phosphate salt is less stimulating/irritating to tongue surface of the body than 5-ALA hydrochloride.

Trichloroacetic acid (TCA) is a small organic acid with a molecular weight greater than acetic acid and hydrochloric acid. It is a potent chemical cauterant and widely used as topical medication and in cosmetic treatment. The acid has proven ability to penetrate deeper layers of skin, coagulate epidermal protein, to destruct and remove damaged skin cells. TCA also exhibits anti-bacterial and anti-inflammatory activities, and further it can stimulate cell division in the basal skin layer to form new cells and uniformly distribute natural skin pigment melanin. Therapeutic outcomes of TCA are often dependent to the depth of its penetration, which is directly proportional to its concentrations applied. Low concentrations of TCA (10-20%) are used as superficial peels or epidermal peels, which penetrate and affect the depth of the epidermis and the interface of the dermis-epidermis. This concentration range is used to treat mild photoaging, melisma, comedonal acne and postinflammatory erythema. Medium-depth peels or dermal peels of TCA (20-50%), extending the penetration through the epidermis to the papillary dermis, are used for the treatment of moderate photoaging, actinic keratosis and mild acne scarring (Di et al, Photodermatol Photoimmunol Photomed. 2015, 233-8). At 50% or higher, deep peels penetrate midreticular dermis to treat external genital wart and acne scar (Yanofsky et al, Expert Rev Dermatol, 2013, 8:321-332; Agarwal et al, Dermatol Surg, 2015, 41:597-604).

Both TCA peeling and 5-ALA or 5-MAL PDT are widely used in dermatology and cosmetic care but often show different therapeutic profiles. For example, in the treatment of acne vulgaris, comedonal acne/noninflammatory lesions respond well to TCA peels, whereas papulopustular acne/inflammatory lesions show moderate improvement (Meguid et al, Dermatol Surg, 2015, 41:1398-1404). In contrast, 5-ALA PDT produces significant improvements in papulopustular acne/inflammatory lesions, but poor responses in comedonal/noninflammatory lesions. The different outcomes may be explained by their mechanism of actions. 5-ALA PDT selectively destructs the sebaceous unit (Wan et al, Clin Cosmed Investig Dermatol, 2014, 7:145-163). The mechanism of TCA in the treatment of acne vulgaris is believed to be due to its ability to diminish corneocyte cohesion and keratinocyte plugging. Therefore, a salt of TCA with 5-ALA or its esters may provide synergistic effects or dual activities in treating acne vulgaris and other diseases or disorders described herein. The present inventors have found that the salts of TCA with 5-ALA or its esters are less irritating/stimulating to the sensitive surface of the body when compared with the hydrochloride salts. The present inventors have also found that TCA salts of 5-MAL and 5-HAL are resistant to moisture and much less hygroscopic than corresponding hydrochloride salts.

SUMMARY

In a first aspect, a salt has formula (I):

$$H_2NCH_2COCH_2CH_2COOR.X—COOH \qquad (I)$$

R and X are defined as below.

In a second aspect, a method of preparing a salt of 5-ALA or derivatives thereof comprises: providing a solution of N-protecting group-5-aminolevulinic acid or derivative thereof; and adding a hydrogenation agent, $H_2$, and X—COOH to provide the salt of 5-ALA or derivatives thereof. X is defined as below.

In a third aspect, a method of preparing a salt of 5-aminolevulinic acid or derivatives thereof comprises: passing 5-aminolevulinic acid or derivatives thereof through a resin; collecting the eluent; and mixing the eluent with X—COOH to provide the salt of 5-aminolevulinic acid or derivatives thereof. X is defined as below.

DETAILED DESCRIPTION

The present disclosure relates to salts of 5-aminolevulinic acid (5-ALA) and its esters, in particular, to trichloroacetic acid salts. The acid selected to form new salts with 5-ALA and its esters as described in the present disclosure may provide a synergistic therapeutic effects or duel actions in PDT. Furthermore, the new salts in the present disclosure possess improved physicochemical properties such as reduced hydroscopicity, important features in manufacture and in quality control during storage, and lower skin irritation than their corresponding hydrochloride salts.

Definitions

When describing the compounds, salts, compositions, methods and processes of this disclosure, the following terms have the following meanings, unless otherwise indicated.

The term "halogen" or "halo" means a chlorine, bromine, iodine, or fluorine atom.

The term "alkyl" means a hydrocarbon group that may be linear, cyclic, or branched or a combination thereof having the number of carbon atoms designated (i.e., $C_{2-12}$ means two to twelve carbon atoms). Examples of alkyl groups include methyl, ethyl, n-propyl, isopropyl, n-butyl, t-butyl, isobutyl, sec-butyl, cyclohexyl, cyclopentyl, (cyclohexyl) methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl groups include haloalkyl, thioalkyl, aminoalkyl, and the like.

The term "alkenyl" means a hydrocarbon group that contains at least one carbon-to-carbon double bond. Alkenyl groups can include, e.g., allyl, 1-butenyl, 2-hexenyl and 3-octenyl groups. Alkenyl groups can be substituted or unsubstituted, unless otherwise indicated.

The term "alkynyl" means a hydrocarbon group that contains at least one carbon-to-carbon triple bond. Alkynyl groups can include, e.g., ethynyl, propargyl, and 3-hexynyl. Alkynyl groups can be substituted or unsubstituted, unless otherwise indicated.

The term "aryl" means a polyunsaturated, aromatic hydrocarbon group having 5-10 atoms and forming a single ring (monocyclic, preferably with 6 atoms such as phenyl) or multiple rings (bicyclic (preferably with 10 atoms such as naphthyl) or polycyclic), which can be fused together or linked covalently. Examples of aryl groups include phenyl and naphthalene-1-yl, naphthalene-2-yl, biphenyl and the like. Aryl groups can be substituted or unsubstituted, unless otherwise indicated.

The term "heteroaryl" means an aromatic group containing 5-10 atoms and at least one heteroatom (such as S, N, O, Si), where the heteroaryl group may be monocyclic (with preferably 5 or 6 atoms) or bicyclic (with preferably 9 or 10 atoms). Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

The term "cycloalkyl" refers to saturated monocyclic, bicyclic, tricyclic, or other polycyclic hydrocarbon groups. Any atom can be substituted, e.g., by one or more substituents. A ring carbon serves as the point of attachment of a cycloalkyl group to another moiety. Cycloalkyl groups can contain fused rings. Fused rings are rings that share a common carbon atom. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "heterocyclyl" or "heterocyclic", which are synonymous as used herein, means a saturated or unsaturated non-aromatic ring containing at least 5-10 atoms (preferably 5 or 6) and at least one heteroatom (typically 1 to 5 heteroatoms) selected from nitrogen, oxygen or sulfur. The heterocyclyl ring may be monocyclic (with preferably 5 or 6 atoms) or bicyclic (with preferably 9 or 10 atoms). The ring system has 1-4 heteroatoms if monocyclic, 1-8 heteroatoms if bicyclic, or 1-10 heteroatoms if tricyclic, the heteroatoms selected from O, N, or S (and mono and dioxides thereof, e.g., N→O⁻, S(O), $SO_2$). The heterocyclyl groups can contain fused rings. Fused rings are rings that share a common carbon atom. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like.

The term "ring" means a compound whose atoms are arranged in formulas in a cyclic form. The ring compound can be either carbocyclic or heterocyclic.

The term "substituent" refers to a group "substituted" on, e.g., an alkyl, cycloalkyl, alkenyl, alkynyl, aralkyl, heteroaralkyl, heterocyclyl, heterocycloalkenyl, cycloalkenyl, aryl, heteroaryl, arylcycloalkyl, heteroarylcycloalkyl, arylcycloalkenyl, heteroarylcycloalkenyl, arylheterocyclyl, heteroarylheterocyclyl, arylheterocycloalkenyl, or heteroarylheterocycloalkenyl group at any atom of that group. In one aspect, the substituent(s) on a group are independently any one single, or any combination of two or more of the permissible atoms or groups of atoms delineated for that substituent. In another aspect, a substituent may itself be substituted with any one of the above substituents.

In general, and unless otherwise indicated, substituent (radical) prefix names are derived from the parent hydride by either (i) replacing the "ane" in the parent hydride with the suffixes "yl," "diyl," "triyl," "tetrayl," etc.; or (ii) replacing the "e" in the parent hydride with the suffixes "yl," "diyl," "triyl," "tetrayl," etc. (here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, allyl, phenyl, and thienyl are also used herein throughout. Conventional numbering/lettering systems are also adhered to for substituent numbering and the nomenclature of fused, bicyclic, tricyclic, polycyclic rings.

In general, when a definition for a particular variable includes both hydrogen and non-hydrogen (halo, alkyl, aryl, etc.) possibilities, the term "substituent(s) other than hydrogen" refers collectively to the non-hydrogen possibilities for that particular variable.

All of the above terms (e.g., "alkyl," "aryl," "heteroaryl" etc.), in some embodiments, include both substituted and unsubstituted forms of the indicated groups. These groups may be substituted multiple times, as chemically allowed.

The term "composition" as used herein is intended to encompass a product comprising the specified ingredients in the specified amounts, as well as any product which results, directly or indirectly, from combination of the specified ingredients in the specified amounts. By "pharmaceutically-acceptable" it is meant the carrier, diluent or excipient must be compatible with the other ingredients of the formulation and not deleterious to the recipient thereof.

The pharmaceutical compositions for the administration of the salts of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Additional excipients, for example sweetening, flavoring and coloring agents, may also be present.

The pharmaceutical compositions of the disclosure may also be in the form of oil in water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents. The salts of the present disclosure may also be administered in the form of suppositories for rectal administration of the drug. These compositions can be prepared by mixing the drug with a suitable nonirritating excipient which is solid at ordinary temperatures but liquid at the rectal temperature and will therefore melt in the rectum to release the drug. Such materials are cocoa butter and polyethylene glycols. Additionally, the salts can be administered via ocular delivery by means of solutions or ointments. Still further, transdermal delivery of the subject salts can be accomplished by means of iontophoretic patches and the like.

For topical use, creams, ointments, jellies, solutions or suspensions containing the disclosed salts are employed. As used herein, topical application is also meant to include the use of mouth washes and gargles.

The pharmaceutical compositions and methods of the present disclosure may further comprise other therapeutically active compounds as noted herein, such as those applied in the treatment of the above mentioned pathological conditions.

"Pharmaceutically acceptable" carrier, diluent, or excipient is a carrier, diluent, or excipient compatible with the other ingredients of the formulation and not deleterious to the recipient thereof.

"Therapeutically effective amount" refers to an amount sufficient to effect treatment when administered to a patient in need of treatment.

"Treating" or "treatment" as used herein refers to the treating or treatment of a disease or medical condition (such as a cancer) in a patient, such as a mammal (particularly a human or a companion animal) which includes:

ameliorating the disease or medical condition, i.e., eliminating or causing regression of the disease or medical condition in a patient;

suppressing the disease or medical condition, i.e., slowing or arresting the development of the disease or medical condition in a patient; or alleviating the symptoms of the disease or medical condition in a patient.

Certain salts of the present disclosure can exist in unsolvated forms as well as solvated forms, including hydrated forms. In general, both solvated forms and unsolvated forms are intended to be encompassed within the scope of the present invention.

Certain salts of the present disclosure may exist in multiple crystalline or amorphous forms (i.e., as polymorphs). In general, all physical forms are equivalent for the uses contemplated by the present disclosure and are intended to be within the scope of the present invention.

The salts of the present disclosure may also contain unnatural proportions of atomic isotopes at one or more of the atoms that constitute such salts. For example, the salts may be radiolabeled with radioactive isotopes, such as for example tritium ($^3$H), iodine-125 ($^{125}$I) or carbon-14 ($^{14}$C). All isotopic variations of the salts of the present invention, whether radioactive or not, are intended to be encompassed within the scope of the present invention.

A salt of formula (I) can be administered alone or in combination with one or more other therapeutic agents, possible combination therapy taking the form of fixed combinations or administration of a compound of the invention and one or more other therapeutic agents being staggered or given independently of one another.

Salts

The present disclosure provides a salt with formula (I):

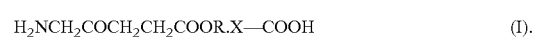

$$H_2NCH_2COCH_2CH_2COOR.X—COOH \qquad (I).$$

R is selected from the group consisting of hydrogen, unsubstituted or substituted alkyl, unsubstituted or substituted alkenyl, unsubstituted or substituted alkynyl, unsubstituted or substituted carbocyclic, unsubstituted or substituted $C_{6-12}$ aryl, unsubstituted or substituted 3-12 membered heterocyclic, and unsubstituted or substituted 5-12 membered heteroaryl.

X is selected from hydrogen, —$CY^1R^1R^2$, —$CY^1Y^2R^1$, and —$CY^1Y^2Y^3$. $Y^1$, $Y^2$, and $Y^3$ are independently selected from F, Cl, Br, and I. $R^1$ and $R^2$ are independently selected from the group consisting of hydrogen, unsubstituted or substituted alkyl, unsubstituted or substituted alkenyl, unsubstituted or substituted alkynyl, unsubstituted or substituted carbocyclic, unsubstituted or substituted $C_{6-12}$ aryl, unsubstituted or substituted 3-12 membered heterocyclic, and unsubstituted or substituted 5-12 membered heteroaryl. $R^1$ and $R^2$ may combine with an atom or atoms to which it is attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl.

In some embodiments, R is hydrogen.

In some embodiments, R is substituted or unsubstituted $C_{1-20}$alkyl. In some embodiments, R is unsubstituted $C_{1-8}$alkyl. In some embodiments, R is selected from the group consisting of methyl, ethyl, propyl, butyl, pentyl, hexyl, sec-propyl, sec-butyl, tert-butyl, sec-pentyl, and sec-hexyl. In some embodiments, R is methyl. In some embodiments, R is hexyl. In some embodiments, R is benzyl. In some embodiments, R is methylbenzyl.

In some embodiments, R is alkyl substituted with at least one selected from the group consisting of hydroxyl, thiol, carboxyl, carbamoyl, ester, amino, alky-amino, amide, halogen, nitro and cyano group.

In some embodiments, R is unsubstituted or substituted carbocyclic. In some embodiments, R is unsubstituted or substituted $C_{3-6}$carbocyclic. In some embodiments, R is selected from the group consisting of cyclopropyl, cyclobutyl, cyclopentyl, and cyclohexyl.

In some embodiments, R is unsubstituted or substituted $C_{6-12}$ aryl. In some embodiments, R is unsubstituted or substituted benzyl. In some embodiments, R is selected from the group consisting of benzyl, 2-methyl benzyl, 4-methyl benzyl, 4-chloro-benzyl, 4-chloro-benzyl, 2-nitro-benzyl, 4-nitro-benzyl, 2-isopropyl benzyl, 4-isopropyl benzyl, 4-fluoro-benzyl, and 4-fluoro-benzyl.

In some embodiments, R is selected from the group consist of hydrogen, methyl, ethyl, propyl, butyl, pentyl, hexyl, sec-propyl, sec-butyl, tert-butyl, sec-pentyl, sec-hexyl, cyclopropyl, cyclobutyl, cyclopentyl, cyclohexyl, benzyl, 2-methyl benzyl, 4-methyl benzyl, 4-chloro-benzyl, 4-chloro-benzyl, 2-nitro-benzyl, 4-nitro-benzyl, 2-isopropyl benzyl, 4-isopropyl benzyl, 4-fluoro-benzyl, and 4-fluoro-benzyl.

In some embodiments, X is —CY$^1$H$_2$. Y$^1$ is Cl or F. In some embodiments, Y$^1$ is Cl. In some embodiments, X is —CY$^1$Y$^2$H. Y$^1$ and Y$^2$ are independently selected from Cl and F. In some embodiments, Y$^1$ and Y$^2$ are Cl. In some embodiments, X is —CY$^1$Y$^2$Y$^3$. Y$^1$, Y$^2$ and Y$^3$ are independently selected from Cl and F. In some embodiments, Y$^1$, Y$^2$ and Y$^3$ are Cl.

In some embodiments, X is selected from the group consisting of —CH$_2$Cl, —CHCl$_2$ and —CCl$_3$. In some embodiments, X is —CCl$_3$. In some embodiments, X is —CH$_2$Cl.

In some embodiments, X—COOH is selected from the group consisting of 2-chloroacetic acid and 2,2,2-trichloroacetic acid.

In some embodiments, the salt is selected from the group consisting of 5-aminolevulinic acid 2,2,2-trichloroacetate, methyl 5-aminolevulinate 2,2,2-trichloroacetate, hexyl 5-aminolevulinate 2,2,2-trichloroacetate, benzyl 5-aminolevulinate 2,2,2-trichloroacetate, 2- or 4-methylbenzyl 5-aminolevulinate 2,2,2-trichloroacetate.

Preferred salts include 5-aminolevulinic acid 2-monochloroacetate, 5-aminolevulinic acid 2.2-dichloroacetate, 5-aminolevulinic acid 2,2,2-trichloroacetate, methyl 5-aminolevulinate 2-monochloroacetate, methyl 5-aminolevulinate 2,2-dichloroacetate, methyl 5-aminolevulinate 2,2,2-trichloroacetate, ethyl 5-aminolevulinate 2-monochloroacetate, ethyl 5-aminolevulinate 2,2-dichloroacetate, ethyl 5-aminolevulinate 2,2,2-trichloroacetate, propyl 5-aminolevulinate 2-monochloroacetate, propyl 5-aminolevulinate 2,2-dichloroacetate, propyl 5-aminolevulinate 2,2,2-trichloroacetate, butyl 5-aminolevulinate 2-monochloroacetate, butyl 5-aminolevulinate 2,2-dichloroacetate, butyl 5-aminolevulinate 2,2,2-trichloroacetate, pentyl 5-aminolevulinate 2-monochloroacetate, pentyl 5-aminolevulinate 2,2-dichloroacetate, pentyl 5-aminolevulinate 2,2,2-trichloroacetate, hexyl 5-aminolevulinate 2-monochloroacetate, hexyl 5-aminolevulinate 2,2-dichloroacetate, hexyl 5-aminolevulinate 2,2,2-trichloroacetate, benzyl 5-aminolevulinate 2-monochloroacetate, benzyl 5-aminolevulinate 2,2-dichloroacetate, benzyl 5-aminolevulinate 2,2,2-trichloroacetate, 2-methylbenzyl 5-aminolevulinate 2-monochloroacetate, 2-methylbenzyl 5-aminolevulinate 2,2-dichloroacetate, 2-methylbenzyl 5-aminolevulinate 2,2,2-trichloroacetate, 4-methylbenzyl 5-aminolevulinate 2-monochloroacetate, 4-methylbenzyl 5-aminolevulinate 2,2-dichloroacetate, 4-methylbenzyl 5-aminolevulinate 2,2,2-trichloroacetate, 4-chlorobenzyl 5-aminolevulinate 2-monochloroacetate, 4-chlorobenzyl 5-aminolevulinate 2,2-dichloroacetate, 4-chlorobenzyl 5-aminolevulinate 2,2,2-trichloroacetate, 4-nitrobenzyl 5-aminolevulinate 2-monochloroacetate, 4-nitrobenzyl 5-aminolevulinate 2,2-dichloroacetate, 4-nitrobenzyl 5-aminolevulinate 2,2,2-trichloroacetate, 4-isopropybenzyl 5-aminolevulinate 2-monochloroacetate, 4-isopropybenzyl 5-aminolevulinate 2,2-dichloroacetate, 4-isopropybenzyl 5-aminolevulinate 2,2,2-trichloroacetate. The ester analogs of 5-ALA described in US patent publication 2015/0191419 can also react with organic acids described in the current disclosure (in particular trichloroacetic acid) to form the salts in the present disclosure. The entire contents of this patent publication are incorporated herein by reference.

Compositions

New salts from the present disclosure can be taken up by cells and converted to endogenous porphyrins with photosensitizing activities, indicating that they are useful therapeutic agents for PDT. These salts can be used either as raw materials or preferably, as pharmaceutical compositions. Thus, according to a further aspect, the present disclosure provides a pharmaceutical composition comprising a compound from the disclosure and at least one pharmaceutically or cosmetically acceptable excipient or carrier and optionally one or more therapeutic ingredients.

In some embodiments, a composition comprises the salt of formula (I) and at least one of a pharmaceutically acceptable carrier and a cosmetically acceptable carrier. In some embodiments, the composition further comprises hydroxyethyl cellulose gel. In some embodiments, the composition comprises the salt of formula (I) and the salt is from about 0.01% to about 95% by weight. In some embodiments, the salt is from about 0.1% to about 50% by weight. In some embodiments, the salt is about 0.1% to about 20% by weight.

In some embodiments, a composition comprises the salt of formula (I) and hydroxylethyl cellulose gel. In some embodiments, the hydroxyethyl cellulose gel has a molecular weight from about 250k to about 725k. In some embodiments, the composition comprises the salt of formula (I) and the salt is from about 0.01% to about 95% by weight. In some embodiments, the salt is from about 0.1% to about 50% by weight. In some embodiments, the salt is about 0.1% to about 20% by weight.

In some embodiments, a composition comprises the salt of formula (I) and a cream, such as Unguentum Merck cream (Almirall Hermal) or Cetaphil@ (Galderma). In some embodiments, the composition comprises the salt of formula (I) and the salt is from about 0.01% to about 99% by weight. In some embodiments, the salt is from about 0.1% to about 50% by weight. In some embodiments, the salt is about 0.1% to about 20% by weight.

In some embodiments, the composition comprises the salt of formula (I) as a first photosensitizing agent, and a second photosensitizing agent. The second photosensitizing agent can be any suitable agent. For example, the second photosensitizing agent is selected from the group consisting of indium-bound pyropheophorbides, pyrrole-derived macrocyclic compounds, porphyrins, chlorins, phthalocyanines, indium chloride methyl pyropheophorbide, naphthalocyanines, porphycenes, porphycyanines, pentaphyrins, sapphyrins, benzochlorins, chlorophylls, azaporphyrins, purpurins, anthracenediones, anthrapyrazoles, aminoanthraquinone, phenoxazine dyes, photofirn, hypocrellins, and derivatives thereof.

Formulations

The salts according to present disclosure may be formulated in any conventional form with one or more pharmaceutically or cosmetically acceptable carrier or excipient suitable for skin, internal surface of the body, oral, intrarectal and system administrations by using the technique well known in the art. All the excipients mentioned herein are commercially available and published in literature (e.g. Hoepfner et al, Fiedler Encyclopedia of Excipients for Pharmaceuticals, Cosmetics and Related Areas, Edition Cantor, Munich, 2002). Topical formulations or compositions are preferred such as powders, solutions, gels, creams, ointments, sprays, lotions, sticks, pessaries, or aerosol sprays. The excipients or carriers in the composition herein described include an aqueous or oil base, thickening or gelling agents, hydrogels, emulsifying, nanoemulsifying, dispersing, solubilizing, stabilizing, suspending, and dispersing agents, coloring agents or propellant. The technique to produce formulations described herein is known in the art and a person skilled in the art will be able to select proper excipients for pharmaceutical or cosmetic compositions of present disclosure.

For oral, parenteral administration or intradermal (e.g. subcutaneous, intraperitoneal or intravenous), the compositions may be formulated as tablets, capsules, suspensions and solutions containing an active component from present disclosure and one or more carriers and/or diluents, including water, ethanol, glycerol, sorbitol, corn starch, lactose, sucrose, microcrystalline cellulose, magnesium stearate, polyvinylpyrrolidone, citric acid, tartaric acid, propyleneglycol, stearylalcohol, propyleneglycol, stearylalcohol, polyethyleneglycol, carboxymethylcellulose or fatty substances, saline and buffer solutions.

The topical formulations can assume any of a variety of dosage forms, including solutions, suspensions, ointments, and solid inserts, hydrogel suppositories. Examples are creams, lotions, gels, ointments, suppositories, sprays, foams, liniments, aerosols, buccal and sublingual tablets, various passive and active topical devices for absorption through the skin and mucous membranes, including transdermal applications, and the like.

Typical pharmaceutically acceptable carriers for topical formulations are, for example, water, mixtures of water and water-miscible solvents such as lower alkanols or vegetable oils, and water-soluble pharmaceutically acceptable non-toxic polymers, for example, alginate, cellulose derivatives such as methylcellulose. A typical cream or ointment-type carrier for topical application that can be used according to the methods and compositions described herein include a mixture of water, glycerin, propylene glycol, and methylparaben. Topical carriers may also include other conventional emulsifiers and emollients including alginates, glyceryl stearate, PEG-100 stearate, cetyl alcohol, propylparaben, butylparaben, sorbitols, polyethoxylated anhydrosorbitol monostearate (TWEEN), white petrolatum (VASELINE), triethanolamine, Emu oil, aloe vera extract, lanolin, cocoa butter, and the like. Suitable topical carriers are well known to the skilled artisan.

For instance, Unguentum Merck (Almirall Hermal) or Cetaphil@ (Galderma) is admixed in the compositions described herein. Typically, the Unguentum Merck base or Cetaphil@ will make up more than about 70% of the total composition and more preferably about 80% of the composition is the cream. Alternative ointment bases are known to persons skilled in the art such as Lipoderm® (PCCA).

In some embodiments, a formulation comprises the salt of formula (I) and a cream, such as Unguentum Merck cream (Almirall Hermal) or Cetaphil@ (Galderma). In some embodiments, the formulation comprises the salt of formula (I) and the salt is from about 0.01% to about 99% by weight. In some embodiments, the salt is from about 0.1% to about 50% by weight. In some embodiments, the salt is about 0.1% to about 20% by weight.

A typical transdermal formulation comprises a conventional aqueous or non-aqueous vehicle, for example, a cream, ointment lotion or paste or in the form of a medicated plaster, patch or membrane.

As used herein, transdermal delivery also includes numerous different systems for the transdermal delivery of active agents known in the art. Transdermal delivery systems include but are not limited to passive devices such as drug-in-adhesive transdermal patches and "active" transdermal technologies such as iontophoresis, electroporation, sonophoresis, magnetophoresis, microneedle devices, needle free injection and those devices that use thermal energy to make the skin more permeable.

The salts and compositions according to present disclosure may be formulated or administered with other photosensitizing agents (e.g. Photofrin, hypocrellins or the like) to enhance treatment efficacies. Other agents may also be used to increase the accumulation and absorption of PpIX, including any chelating agents published in the literature (such as EDTA, CDTA and the like) to chelate ferrous ions blocking the conversion of PpIX to heme; and any surface-penetration assisting agents described in the literatures (such as DMSO, surfactants or non-surfactants, fatty acids, and bile salts) may be applicable to enhance absorption of salts from the present disclosure.

The surface penetration agent may be used in a concentration range of about 0.2 to about 50% (weight/volume), e.g. about 5%.

The chelating agent may be provided at a concentration of about 0.05 to about 20% (weight/volume), e.g. about 0.1 to about 5%.

The compositions described herein can further comprise non-physiologically active ingredients or components usually admixed in such topical preparations. For example, the compositions may also include additional ingredients such as other carriers, moisturizers, oils, fats, waxes, surfactants, thickening agents, antioxidants, viscosity stabilizers, chelating agents, buffers, preservatives, perfumes, dyestuffs, lower alkanols, humectants, emollients, dispersants, antibacterials, antifungals, disinfectants, vitamins, antibiotics, or other anti-acne agents, as well as other suitable materials that do not have a significant adverse effect on the activity of the topical composition. Additional inactive ingredients for inclusion in the carrier may be sodium acid phosphate moisturizer, witch hazel extract carrier, glycerin humectant, apricot kernel oil emollient, corn oil dispersant, and the like which are further detailed below. Those of skill in the art will readily recognize additional inactive ingredients, which can be admixed in the compositions described herein.

Kit

A kit for photodynamic therapy or diagnosis comprises a first container comprising a pharmaceutically or cosmetically effective amount of salt of formula (I) or composition thereof, and a second container comprising a dissolution medium. The second container can further comprise at least one of a carrier, a chelating agent including EDTA, CDTA and a surface penetration agent such as DMSO, surfactants or non-surfactants, fatty acids or bile salts.

Surface penetration agents can be included in some embodiments to optimize transfer of the salt of formula (I) through the stratum corneum and into the dermis/dermatome to provide a local effect. For a discussion of use of penetration enhancers in topical formulations see generally, Percutaneous Penetration Enhancers (Eric W. Smith & Howard I. Maibach eds. 1995); Ghosh, T. K. et al. 17 Pharm. Tech. 72 (1993); Ghosh, T. K. et al. 17 Pharm. Tech. 62 (1993); Ghosh, T. K. et al. 17 Pharm. Tech. 68 (1993), all of which citations are hereby incorporated herein by reference. The penetration agents should be pharmacologically inert, non-toxic, and non-allergenic, have rapid and reversible onset of action, and be compatible with the compositions of the invention.

Examples of penetration agents include, but are not limited to ethyl alcohol, isopropyl alcohol, lauryl alcohol, salicylic acid, octolyphenylpolyethylene glycol, polyethylene glycol 400, propylene glycol, N-decylmethylsulfoxide, DMSO and the azacyclo compounds, as disclosed in U.S. Pat. Nos. 4,755,535; 4,801,586; 4,808,414; and 4,920,101, all of which patents are hereby expressly incorporated herein by reference.

In one embodiment, the dissolution medium is an aqueous or non-aqueous medium. In one embodiment, the dissolution medium is sodium chloride solution. In some embodiments, the aqueous solution is about 0.9% sodium chloride solution. In some embodiments, the aqueous solution is a buffer solution. In some embodiments, the aqueous solution is phosphate-buffered saline.

In some embodiments, the salt of formula (I) is a first photosensitizing agent, and the second container comprises a second photosensitizing agent. The second photosensitizing agent can be any suitable agent. In some embodiments, the second photosensitizing agent is selected from the group consisting of indium-bound pyropheophorbides, pyrrole-derived macrocyclic compounds, porphyrins, chlorins, phthalocyanines, indium chloride methyl pyropheophorbide, naphthalocyanines, porphycenes, porphycyanines, pentaphyrins, sapphyrins, benzochlorins, chlorophylls, azaporphyrins, purpurins, anthracenediones, anthrapyrazoles, aminoanthraquinone, phenoxazine dyes, photofirn, hypocrellins, and derivatives thereof.

Methods of Treatment

In one aspect, the present disclosure provides a method of administering the new salts of formula (I) or compositions of formular (I) extracellularly, intracellular photosensitizer porphyrins (in particular PpIX) at the treated site are produced via the porphyrin biosynthesis pathway. Subsequent light activation of porphyrins at the treated site can induce cytotoxicity. Thus the salts and their pharmaceutical compositions from the present disclosure can be used in PDT treating diseases or disorders of internal and external surfaces of the body.

The internal and external surface of the body described herein include skin, all epithelial and mucosa surfaces, such as skin and conjunctiva, lining of the nasal passages, nasal sinuses, trachea, bronchi, lining of the mouth, pharynx, oesophagus, stomach, intestines, rectum, and anal canal; lining of the ureters, urinary bladder, and urethra; and lining of the vagina, uterine cervix, and uterus.

In another aspect, the new salts from the present disclosure possess a number of advantages over their corresponding hydrochloride salts that are currently used in the clinic. The salts from the present disclosure are less hygroscopic than hydrochloride salts of 5-ALA or its esters, an important parameter to reduce degradations associated with water content for long term storage and to establish consistent quality controls in manufacture. The salts from the present disclosure are less irritating to the skin. When administrations to sensitive surfaces such as urethra, rectal, vagina and uterine cervix, reduced skin irritating is desirable especially when multiple treatments are needed. In the measurement of fluorescence production in cells, the activity of salts of the present disclosure is similar to that of corresponding hydrochloride salts. Further, acids in the new salts from the present disclosure such as TCA may provide duel activity and/or enhance skin penetration of 5-ALA or its esters in PDT.

In some embodiments, a method of photodynamic therapy to treat a target area in a subject, comprises: administering an effective amount of the salt of formula (I) or the composition comprising salt of formula (I) to the target area; waiting for a time period for adequate absorption and conversion of the salt of formula (I) or the composition comprising salt of formula (I) to PpIX; exposing the target area to a light with an amount and a wavelength effective to induce cytotoxicity; thereby administering photodynamic therapy to the target tissue in the subject.

In some embodiments, the wavelength is from about 400 to about 1000 nm. In some embodiments, the wavelength is from about 380 to about 440 nm. In some embodiments, the wavelength from about 620 to about 750 nm.

In some embodiments, the target tissue is skin, and the method is used to treat a dermatological disorder.

In some embodiments, the target tissue is skin, and the method is used for cosmetic treatment of skin conditions. The skin conditions comprise diffuse or mottled pigmentation, rosacea, sebaceous hyperplasia, photoaging, rough sun damaged skin, wrinkles, enlarged pores and skin texture, acne, acne scar, tactile roughness, sallowness and dull skin.

In some embodiments, the method is used for skin rejuvenation.

In some embodiments, the method is used to treat cancers, basal cell carcinoma, cervical intraepithelial neoplasia, actinic keratosis, Bowen's disease, vulvar Paget's disease, acne, acne vulgaris, psoriasis, nevus flammeus, lupus erythematosus, condyloma acuminata, refractory palmoplantar wart, cutaneous T cell lymphoma, bacterial infections, fungal infections, inflammation disorders and virus infections.

In some embodiments, the method is used to promote hair growth, tissue repair and wound healing.

In some embodiments, the cancers comprise bladder cancer, colorectal cancer, lung cancer, brain cancer, stomach cancer, uterine cancer, skin cancer, and oral cancers, rectal cancers and cholangiocarcinoma.

The administration of formula (I) or composition thereof is by an oral route, organ Instillation, parenteral injection, needle free injection or by a topical route.

The light sources may be lamps (e. g. fluorescent lamps), lasers, light emitting diodes (LED) or filtered intense pulse lights. Optical fibers may be used to reach inaccessible regions. The light wavelength may be in the range of about 300 to about 1200 nm, and preferably, about 380 to about 800 nm. The dose level of irritation would be about 5 to about 200 J/cm$^2$, and preferably, about 10 to about 120 J/cm$^2$. Daylight may also be applied as an alternative light source (Rubel et al, Br J Dermatol, 2014, 171, 1164-1171). The time interval (incubation time) between drug application and exposure to light may be about 0.1 to about 24 hours, and preferably, from about 0.3 to about 4 hours. For PDD, a red light (e.g. 600-750 nm) is first used to examine the target area and then a blue light (e.g. 380-440 nm) to evaluate fluorescence levels.

The concentration of the salt in the composition may be about 0.01 to about 95% (w/w or w/v), and preferably, about 0.1 to about 50% (w/w), about 0.1 to about 30%, or about 0.1 to about 20%. The effective dose may be determined according to factors such as age, weight, lesion area, and conditions of diseases, or different purposes (e.g. cosmetic, treatment or diagnosis). In general, the effective dosage would be in the range of about 0.001 to about 3 g/day, and preferably, in the range of about 0.01 to about 2 g/day.

The exemplary salts for treatment are 5-aminolevulinic acid 2-monochloroacetate, 5-aminolevulinic acid 2,2-dichloroacetate, 5-aminolevulinic acid 2,2,2-trichloroacetate, methyl 5-aminolevulinate 2-monochloroacetate, methyl 5-aminolevulinate 2,2-dichloroacetate, methyl 5-aminolevulinate 2,2,2-trichloroacetate, ethyl 5-aminolevulinate 2-monochloroacetate, ethyl 5-aminolevulinate 2,2-dichloroacetate, ethyl 5-aminolevulinate 2,2,2-trichloroacetate, propyl 5-aminolevulinate 2-monochloroacetate, propyl 5-aminolevulinate 2,2-dichloroacetate, propyl 5-aminolevulinate 2,2,2-trichloroacetate, butyl 5-aminolevulinate 2-monochloroacetate, butyl 5-aminolevulinate 2,2-dichloroacetate, butyl 5-aminolevulinate 2,2,2-trichloroacetate, pentyl 5-aminolevulinate 2-monochloroacetate, pentyl 5-aminolevulinate 2,2-dichloroacetate, pentyl 5-aminolevulinate 2,2,2-trichloroacetate, hexyl 5-aminolevulinate 2-monochloroacetate, hexyl 5-aminolevulinate 2,2-dichloroacetate, hexyl 5-aminolevulinate 2,2,2-trichloroacetate, benzyl 5-aminolevulinate 2-monochloroacetate, benzyl 5-aminolevulinate 2,2-dichloroacetate, benzyl 5-aminolevulinate 2,2,2-trichloroacetate, 2-methylbenzyl 5-aminolevulinate 2-monochloroacetate, 2-methylbenzyl 5-aminolevulinate 2,2-dichloroacetate, 2-methylbenzyl 5-aminolevulinate 2,2,2-trichloroacetate, 4-methylbenzyl 5-aminolevulinate 2-monochloroacetate, 4-methylbenzyl 5-aminolevulinate 2,2-dichloroacetate, 4-methylbenzyl 5-aminolevulinate 2,2,2-trichloroacetate, 4-chlorobenzyl 5-aminolevulinate 2-monochloroacetate, 4-chlorobenzyl 5-aminolevulinate 2,2-dichloroacetate, 4-chlorobenzyl 5-aminolevulinate 2,2,2-trichloroacetate, 4-nitrobenzyl 5-aminolevulinate 2-monochloroacetate, 4-nitrobenzyl 5-aminolevulinate 2,2-dichloroacetate, 4-nitrobenzyl 5-aminolevulinate 2,2,2-trichloroacetate, 4-isopropybenzyl 5-aminolevulinate 2-monochloroacetate, 4-isopropybenzyl 5-aminolevulinate 2,2-dichloroacetate, 4-isopropybenzyl 5-aminolevulinate 2,2,2-trichloroacetate.

Methods of Diagnosis

In a further aspect, the salt or its composition from present disclosure can be used for an in vivo cancer tissue detection assisting surgeons to resect tumor tissue more effectively, or for an in vitro diagnoses of diseases or disorders by examining body fluid or tissue.

In some embodiments, a method of in vivo diagnosis comprises: administering the salt of formula (I) or composition thereof to a subject; waiting for a time period (e.g. 1-4 hours) allowing adequate absorption and conversion of said agents to photosensitizers, exposing the target area to a light having a wavelength of about 380 to about 440 nm; and detecting areas with enhanced fluorescence levels. In some embodiments, the fluorescence levels are fluorescence spectra. In some embodiments, the fluorescence levels are fluorescence images.

In some embodiments, a method of in vitro diagnosis of diseases in a subject, comprises: providing a sample from a subject, incubating the salt of formula (I) or the composition thereof with the sample to provide a mixture; exposing the mixture to a light having a wavelength of about 380 to about 440 nm; and comparing the fluorescence level with control references.

In some embodiments, the sample is body fluid or a tissue.

In some embodiments, the sample is selected from the group consisting of blood, urine, semen, stool, tears, sputum, spinal fluid, bone marrow, and biopsy tissues.

Preparation

In another aspect, the present disclosure provides a process for preparing the salts of present disclosure comprising reacting 5-ALA or its esters with an acid (e.g. trichloroacetic acid). In the case of using hydrochloride salts as the starting materials, a base can be used to neutralize before adding the acid described in present disclosure.

Thus, a hydrochloride salt of 5-ALA or its esters is treated with a base, followed by reacting with an acid from present disclosure to yield the desired salt as described in Example 1.

Another process to yield the desired salts from present disclosure was to remove N-protecting group of 5-ALA or its ester derivatives in the presence of an acid from present disclosure (e.g. trichloroacetic acid). The starting material may have an N-Boc (N-tert-butyloxycarbonyl) or an N-Cbz (N-carboxybenzyl) protecting group. Thus, reaction can be carried out in one-pot to remove protecting group, followed by formation of the desired salt as described in Example 3 and Example 4. The starting materials in this aspect were 5-N-Boc-aminolevulinic acid, N—Bn or 5-N-Cbz-aminolevulinic acid, or their corresponding ester derivatives (e.g. 5-N-Boc-aminolevulinate methyl ester, 5-N-Boc-aminolevulinate hexyl ester, 5-N-Cbz-aminolevulinate methyl ester, and 5-N-Cbz-aminolevulinate hexyl ester). Catalysts for use to remove Cbz or Bn protecting groups include palladium, platinum, Raney nickel or the like as known in the art.

In some embodiments, a method of preparing a salt of 5-aminolevulinic acid or derivatives thereof, comprises: providing a solution of N-protecting group-5-aminolevulinic acid or derivative thereof; and adding a hydrogenation agent, $H_2$, and X—COOH to provide the salt of 5-aminolevulinic acid or derivatives thereof.

X is selected from hydrogen, $-CY^1R^1R^2$, $-CY^1Y^2R^1$, and $-CY^1Y^2Y^3$. $Y^1$, $Y^2$, and $Y^3$ are independently selected from F, Cl, Br, and I. $R^1$ and $R^2$ are independently selected from the group consisting of hydrogen, unsubstituted or substituted alkyl, unsubstituted or substituted alkenyl, unsubstituted or substituted alkynyl, unsubstituted or substituted carbocyclic, unsubstituted or substituted $C_{6-12}$ aryl, unsubstituted or substituted 3-12 membered heterocyclic, and unsubstituted or substituted 5-12 membered heteroaryl. $R^1$ and $R^2$ may combine with an atom or atoms to which it is attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl.

In some embodiments, the protecting group is carboxybenzyl. In some embodiments, the hydrogenation agent is palladium on carbon.

Additional process provided by present disclosure is ion exchange technique, a standard method to form salts well known in the art. Either acidic ion exchange resins or basic ion exchange resins may be used, and preferably, basic ion exchange resins such as Amberlyst A26(OH). When starting materials are in salt forms such as a hydrochloride salt (e.g. 5-ALA methyl ester hydrochloride), the Cl$^-$ can be exchanged for a basic ion such as OH$^-$ and the resulting eluent can be mixed with an acid from present disclosure to produce the target salt. In general, the ion exchange process involves eluting the 5-ALA salt solution through a column packed with a strong basic ion exchange resin Amberlyst A26(OH) to remove Cl$^-$ and sequentially mixing the eluent with an acid from the present disclosure. Alternatively, this can also be achieved by stirring a solution of 5-ALA ester hydrochloride in the presence of a basic ion exchange resin, [e.g. Amberlyst A26(OH)]. After removal of the resin, an acid from present disclosure is added to the filtrate. These resins are commercially available and operations involved are well known in the art.

The starting materials to make the salts of present disclosure are commercially available or may be prepared by methods published in literatures. Reactions from present disclosure can be carried out in one solvent or a mixture of solvents such as acetone, methanol, ethanol, propanol, isopropanol, butanol, isobutanol, dichloromethane, chloroform, ethyl acetate, ether, hexane, petroleum ether, tetrahydrofuran, N,N-dimethyl formamide or dimethyl sulphoxide or the like, which are well known in the art. The new salts from present disclosure can be purified by crystallization or triturating using a solvent or a mixture of solvents mentioned above. The reaction temperature may be from about −15 to about 100° C. and optimal conditions are chosen according to solvents used and reactions.

In some embodiments, a method of preparing a salt of 5-aminolevulinic acid or derivatives thereof, comprises: passing 5-aminolevulinic acid or derivatives thereof through a resin; collecting the eluent; and mixing the eluent with X—COOH to provide the salt of 5-aminolevulinic acid or derivatives thereof. X is selected from hydrogen, —$CY^1R^1R^2$, —$CY^1Y^2R^1$, and —$CY^1Y^2Y^3$. $Y^1$, $Y^2$, and $Y^3$ are independently selected from F, Cl, Br, and I. $R^1$ and $R^2$ are independently selected from the group consisting of hydrogen, unsubstituted or substituted alkyl, unsubstituted or substituted alkenyl, unsubstituted or substituted alkynyl, unsubstituted or substituted carbocyclic, unsubstituted or substituted $C_{6-12}$ aryl, unsubstituted or substituted 3-12 membered heterocyclic, and unsubstituted or substituted 5-12 membered heteroaryl. $R^1$ and $R^2$ may combine with an atom or atoms to which it is attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl.

In some embodiments, the resin is a basic ion exchange resin.

The following examples are illustrative, but not limiting, of the method and composition of the present disclosure.

EXAMPLES

Example 1

Methyl 5-Aminolevulinate 2,2,2-Trichloroacetate (5-MAL TCA)

To a suspension of ethyl acetate (50 mL) and water (20 mL) was added methyl 5-aminolevulinate hydrochloride (1.8 g, 10 mmol) and $NaHCO_3$ (1.7 g, 20 mmol). The free base was extracted to the organic layer and the aqueous layer extracted twice with ethyl acetate (30 mL×2). The combined ethyl acetate solution was dried over $Na_2SO_4$. After filtration, trichloroacetic acid (1.6 g, 10 mmol) was added to the filtrate and the solution was concentrated to dryness to yield methyl 5-MAL TCA as a white solid (1.7 g, 55%). $^1$HNMR ($D_2O$, 360 MHz) δ ppm: 2.62 (t, j=6 Hz, 2H), 2.82 (t, j=6 Hz, 2H), 3.60 (s, 3H), 4.03 (s, 2H).

Example 2

Hexyl 5-Aminolevulinate 2,2,2-Trichloroacetate (5-HAL TCA)

Hexyl 5-aminolevulinate hydrochloride (2.5 g, 10 mmol) was dissolved in 50% aqueous ethanol (10 mL) and this solution was passed through a column packed with Amberlyst 26(OH) (5 g) into a solution of trichloroacetic acid (1.6 g, 10 mmol) in ethanol (5 mL). The column was washed with 50% aqueous ethanol (20 mL) and combined eluents were evaporated to dryness to give 5-HAL TCA as a white solid (2.1 g, 56%). $^1$HNMR ($D_2O$, 360 MHz) δ ppm: 0.77 (t, j=6 Hz, 3H), 1.21 (br, 6H). 1.53 (m, 2H), 2.62 (t, j=6 Hz), 2H), 2.83 (t, j=6 Hz, 2H), 4.03 (m, 4H).

Example 3

5-Aminolevulinic Acid 2,2,2-Trichloroacetate (5-ALA TCA)

To a solution of 5-N-Cbz-aminolevulinic acid (2.7 g, 10 mmol) in methanol (35 mL) was added palladium on carbon (10%, 0.5 g) and trichloroacetic acid (1.6 g, 10 mmol). The reaction was stirred under $H_2$ atmosphere for 24 hours. The reaction solution was filtered and concentrated to give 5-ALA TCA as a white solid (2.7 g, 92%). $^1$HNMR ($D_2O$, 360 MHz) δ ppm: 2.65 (t, j=6 Hz, 2H), 2.85 (t, j=6 Hz, 2H), 4.03 (s, 2H).

Example 4

Ethyl 5-Aminolevulinate 2,2,2-Trichloroacetate

To a solution of 5-N-Boc-aminolevulinate ethyl ester (2.6 g, 10 mmol) in tetrahydrofuran (20 mL) was added trichloriacetic acid (1.6 g, 10 mmol). The reaction was stirred at 60° C. for 2 hours. The reaction solution was concentrated to offer ethyl 5-aminolevulinate trichloroacetate as a white solid (2.5 g, 78%). $^1$HNMR ($D_2O$, 360 MHz) δ ppm: 1.23 (t, j=7 Hz, 3H). 2.64 (t, j=6 Hz, 2H), 2.83 (t, j=6 Hz, 2H), 4.03 (m, 4H).

The following salts of the present disclosure can be prepared by using the general methods described in Example 1 to Example 4: 5-aminolevulinic acid 2-monochloroacetate, 5-aminolevulinic acid 2,2-dichloroacetate 5-aminolevulinic acid 2,2,2-trichloroacetate, methyl 5-aminolevulinate 2-monochloroacetate, methyl 5-aminolevulinate 2,2-dichloroacetate, methyl 5-aminolevulinate 2,2,2-trichloroacetate, ethyl 5-aminolevulinate 2-monochloroacetate, ethyl 5-aminolevulinate 2,2-dichloroacetate, ethyl 5-aminolevulinate 2,2,2-trichloroacetate, propyl 5-aminolevulinate 2-monochloroacetate, propyl 5-aminolevulinate 2,2-dichloroacetate, propyl 5-aminolevulinate 2,2,2-trichloroacetate, butyl 5-aminolevulinate 2-monochloroacetate, butyl 5-aminolevulinate 2,2-dichloroacetate, butyl 5-aminolevulinate 2,2,2-trichloroacetate, pentyl 5-aminolevulinate 2-monochloroacetate, pentyl 5-aminolevulinate 2,2-dichloroacetate, pentyl 5-aminolevulinate 2,2,2-trichloroacetate, hexyl 5-aminolevulinate 2-monochloroacetate, hexyl 5-aminolevulinate 2,2-dichloroacetate, and hexyl 5-aminolevulinate 2,2,2-trichloroacetate.

The following salts of the present disclosure can be prepared by using the general methods described in Example 1, 2 and 4: benzyl 5-aminolevulinate 2-monochloroacetate, benzyl 5-aminolevulinate 2,2-dichloroacetate, benzy 5-aminolevulinate 2,2,2-trichloroacetate, 2-methylbenzyl 5-aminolevulinate 2-monochloroacetate, 2-methylbenzyl 5-aminolevulinate 2,2-dichloroacetate, 2-methylbenzyl 5-aminolevulinate 2,2,2-trichloroacetate, 4-methylbenzyl 5-aminolevulinate 2-monochloroacetate, 4-methylbenzyl 5-aminolevulinate 2,2-dichloroacetate, 4-methylbenzyl 5-aminolevulinate 2,2,2-trichloroacetate, 4-chlorobenzyl 5-aminolevulinate 2-monochloroacetate, 4-chlorobenzyl 5-aminolevulinate 2,2-dichloroacetate, 4-chlorobenzyl 5-aminolevulinate 2,2,2-trichloroacetate, 4-nitrobenzyl 5-aminolevulinate 2-monochloroacetate, 4-nitrobenzyl 5-aminolevulinate 2,2-dichloroacetate, 4-nitrobenzyl 5-aminolevulinate 2,2,2-trichloroacetate, 4-isopropybenzyl 5-aminolevulinate 2-monochloroacetate, 4-isopropybenzyl 5-aminolevulinate 2,2-dichloroacetate, and 4-isopropybenzyl 5-aminolevulinate 2,2,2-trichloroacetat.

Example 5

Measurement of Hydroscopicity

Hydroscopicity of salts from present disclosure was measured using a weight change method. The test samples were placed in a sealed container with moisture of 70-85% at ambient temperature for 24 hours and their weigh change was measured. All three hydrochloride salts of 5-ALA, 5-MAL and 5-HAL, and 5-ALA TCA were hygroscopic, their weight was increased by 25~75%. These samples turned to a liquid due to deliquescence. The weight of 5-HAL TCA remained unchanged and 5-MAL TCA had minimum weight increase (<5%). The appearance of both samples was unchanged as crystalline solid. These results indicate that the 5-MAL TCA and 5-HAL TCA are resistant to moisture, a desired property for quality control in manufacture and for storage to minimize degradations caused by moisture.

Example 6

Measurement of Potential Skin Irritation/Stimulation

The potential irritation/stimulation of test samples was carried out by applying 3 mg of each sample to the upper surface of the tongue for 3-5 minutes and then evaluated. Results show that the new salts from the present disclosure are less irritation/stimulation than hydrochloride salts of 5-ALA or its esters (Table 1, four participants).

TABLE 1

Measurement of irritation/stimulation on tongue surface.

|  | 1 | 2 | 3 | 4 |
|---|---|---|---|---|
| 5-ALA HCl | D | C | D | C |
| 5-ALA TCA | B | B | B | B |
| 5-MAL HCl | C | C | C | C |
| 5-MAL TCA | B | B | B | B |
| 5-HAL HCl | B | C | C | B |
| 5-HAL TCA | B | B | A | B |

A: no irritation, B: irritation, C: strong irritation, D: very strong irritation.

Example 7

Measurement of PpIX Formation in Cancer Cells

Test samples were dissolved with sterile saline to a concentration of 100 mM as stock solution. The stock solution was diluted to desired concentrations with culture medium or phosphate buffered solution (PBS).

A549 cells (ATCC), derived from human lung carcinoma, were grown in F12 medium (Gibco) containing 4.5 g/L glucose, 10% FCS, and penicillin/streptomycin, at 37° C. and 6% $CO_2$ in a humid environment. For measurement purposes, the cells were sub-cultured in 48-well or 96-well dishes to give $5 \times 10^4$ cells/well 24 hours prior to incubation with test salts. The cells were washed twice with PBS and test solutions were added to the culture. After cells were incubated for 4, 8 or 24 hours, the medium was detached and the plates were rinsed twice with PBS, and PpIX natural fluorescence was measured at 360±40 nm excitation and 620±40 nm emission (CytoFluor Series 4000, Perspective Biosystems, MA, USA). The experiment was conducted in triplets.

Fluorescence production induced by salts from present disclosure was observed and the fluorescence production induced by the salts from present disclosure is similar to that of corresponding hydrochloride salts (Table 2).

TABLE 2

Measurement of PpIX formation in A549 cells in vitro

| Salts | Activity* | | |
|---|---|---|---|
|  | 4 hrs | 8 hrs | 24 hrs |
| 5-ALA HCl (10 mM) | 1.00 | 1.42 ± 0.04 | 2.35 ± 0.19 |
| 5-ALA TCA (10 mM) | 1.00 ± 0.02 | 1.30 ± 0.06 | 2.50 ± 0.17 |
| 5-MAL HCl (10 mM) | 1.27 ± 0.04 | 1.60 ± 0.12 | 2.22 ± 0.16 |
| 5-MAL TCA (10 mM) | 1.20 ± 0.04 | 1.25 ± 0.02 | 2.20 ± 0.16 |
| 5-HAL HCl (0.5 mM) | 1.20 ± 0.15 | 1.57 ± 0.08 | 2.92 ± 0.30 |
| 5-HAL TCA (0.5 mM) | 1.15 ± 0.05 | 1.57 ± 0.11 | 2.72 ± 0.10 |
| 5-HAL HCl (1 mM) | ~2 | ~4 | ~10 |
| 5-HALTCA (1 mM) | ~2 | ~4 | ~10 |

*Relative activity to induce porphyrin formation

Example 8

Solution Formulation 1

5-HAL TCA (250 mg) was dissolved in 0.9% of sodium chloride aqueous solution (5 mL) to form a solution of 5% 5-HAL TCA. Similar solution formulations may be prepared using buffers (such as PBS) for different treatment purposes.

Example 9

Solution Formulation 2

5-HAL TCA (250 mg) was dissolved in 0.9% of sodium chloride aqueous solution (5 mL) containing tricloroacetic acid (100 mg) to form a solution of 5% 5-ALA hexyl ester TCA containing 2% trichloroacetic acid.

Example 10

Gel Formulation 1

Hydroxyethyl cellulose Gel (4.37 g, 1-2%, MW 725,000 or 250,000) was added to 5-ALA TCA (630 mg) with stirring to provide a clear gel of 5-ALA TCA (126 mg/g).

Example 11

Gel Formulation 2

Hydroxyethyl cellulose Gel (4.37 g, 1-2%, MW 725,000 or 250,000) containing TCA (50 mg) was added to 5-ALA TCA (630 mg) with stirring to give a clear gel of 125 mg/g 5-ALA TCA, containing 1% TCA.

Example 12

Cream Formulation 1

5-MAL TCA (1.5 g) was mixed thoroughly with Ung. Merck (8.5 g) to yield a pale to light yellow cream of 150 mg/g 5-MAL TCA.

Example 13

Cream Formulation 2

5-MAL TCA (1.5 g) was mixed thoroughly with Cetaphil@ (8.2 g) and TCA (0.3 g) to yield a pale to light yellow cream of 150 mg/g 5-MAL TCA, containing 3% TCA.

Example 14

Cream Formulation 3

5-MAL TCA (1 g) was mixed thoroughly with Cetaphil® (9 g), which contains 1% DMAO, to yield a pale to light yellow cream of 0.1 g/g 5-MAL TCA containing 1% DMSO.

ABBREVIATIONS USED IN THE PRESENT DISCLOSURE

5-ALA: 5-aminoalevulinic acid
Boc: tert-butyloxycarbonyl
Bn: benzyl
Cbz: carboxybenzyl
EDTA: ethylenediaminetetraacetic acid
CDTA: trans-1,2-Cyclohexanediaminetetraacetic acid
TCA: trichloroacetic acid
DMSO: dimethyl sulphoxide
5-HAL: hexyl 5-aminolevulinate or 5-hexaminolevulinate
5-MAL: methyl 5-aminolevulinate or 5-methylaminolevulinate
HCl: hydrochloric acid
PDT: photodynamic therapy
PDD: photodynamic diagnosis
PpIX: protoporphyrin IX
PBS: phosphate buffered saline

The invention claimed is:

1. A salt having formula (I):

$$H_2NCH_2COCH_2CH_2COOR \cdot Cl_3C-COOH \quad (I)$$

wherein R is selected from the group consisting of hydrogen, methyl, ethyl, propyl, butyl, pentyl, hexyl, sec-propyl, sec-butyl, tert-butyl, sec-pentyl, sec-hexyl, cyclopropyl, cyclobutyl, cyclopentyl, cyclohexyl, benzyl, 2-methylbenzyl, 4-methylbenzyl, 4-chloro-benzyl, 2-nitro-benzyl, 4-nitro-benzyl, 2-isopropylbenzyl, 4-isopropylbenzyl, and 4-fluoro-benzyl.

2. The salt of claim 1, wherein R is selected from the group consisting of hydrogen, methyl.

3. A salt of claim 1 selected from the group consisting of 5-aminolevulinic acid 2,2,2-trichloroacetate, methyl 5-aminolevulinate 2,2,2-trichloroacetate, hexyl 5-aminolevulinate 2,2,2-trichloroacetate, benzyl 5-aminolevulinate 2,2,2-trichloroacetate, and 4-methylbenzyl 5-aminolevulinate 2,2,2-trichloroacetate.

4. A pharmaceutical composition comprising the salt of claim 1 and at least one pharmaceutically or cosmetically acceptable carrier or an excipient.

5. A salt of claim 1, wherein the salt is 5-aminolevulinic acid 2,2,2-trichloroacetate.

6. A salt of claim 1, wherein the salt is methyl 5-aminolevulinate 2,2,2-trichloroacetate.

7. A salt of claim 1, wherein the salt is hexyl 5-aminolevulinate 2,2,2-trichloroacetate.

8. A salt of claim 1, wherein the salt is benzyl 5-aminolevulinate 2,2,2-trichloroacetate.

9. A salt of claim 1, wherein the salt is 4-methylbenzyl 5-aminolevulinate 2,2,2-trichloroacetate.

10. The pharmaceutical composition of claim 4, wherein the salt is selected from the group consisting of 5-aminolevulinic acid 2,2,2-trichloroacetate, methyl 5-aminolevulinate 2,2,2-trichloroacetate, hexyl 5-aminolevulinate 2,2,2-trichloroacetate, benzyl 5-aminolevulinate 2,2,2-trichloroacetate, and 4-methylbenzyl 5-aminolevulinate 2,2,2-trichloroacetate.

11. The pharmaceutical composition of claim 4, wherein the salt is 5-aminolevulinic acid 2,2,2-trichloroacetate.

12. The pharmaceutical composition of claim 4, wherein the salt is methyl 5-aminolevulinate 2,2,2-trichloroacetate.

13. The pharmaceutical composition of claim 4, wherein the salt is hexyl 5-aminolevulinate 2,2,2-trichloroacetate.

* * * * *